United States Patent [19]

Sieving et al.

[11] Patent Number: 5,364,613
[45] Date of Patent: Nov. 15, 1994

[54] POLYCHELANTS CONTAINING MACROCYCLIC CHELANT MOIETIES

[76] Inventors: Paul F. Sieving, 3166 Impala Dr. #5, San Jose, Calif. 95117; Alan D. Watson, 262A Rincon Ave., Campbell, Calif. 95008; Steven C. Quay, 428 Oakmead Pkwy., Sunnyvale, Calif. 94086; Scott M. Rocklage, 255 Cresci Rd., Los Gatos, Calif. 95030

[21] Appl. No.: 464,865

[22] Filed: Jan. 16, 1990

Related U.S. Application Data

[63] Continuation-in-part of Ser. No. 335,162, Apr. 7, 1989, abandoned.

[51] Int. Cl.$^5$ .............. A61K 49/00; A61K 37/00; A61K 39/00; A61K 49/04
[52] U.S. Cl. ............................ 424/9; 424/4; 514/2
[58] Field of Search ............. 530/389.3, 391; 514/2; 424/4, 9, 85.8

[56] References Cited

U.S. PATENT DOCUMENTS

| | | | |
|---|---|---|---|
| 3,927,193 | 12/1975 | Hansen et al. | 424/1 |
| 4,167,173 | 11/1979 | Winchell et al. | 424/4 |
| 4,331,647 | 5/1982 | Goldenberg | 424/1 |
| 4,639,365 | 1/1987 | Sherry | 424/9 |
| 4,647,447 | 3/1987 | Gries et al. | 424/9 |
| 4,678,667 | 7/1987 | Meares et al. | 424/85 |
| 4,741,900 | 5/1988 | Alvarez et al. | 514/2 |
| 4,806,348 | 2/1989 | Hartl et al. | 530/389.3 |
| 4,855,353 | 8/1989 | Kurami et al. | 525/54.1 |
| 5,098,692 | 3/1992 | Gries et al. | 424/9 |
| 5,135,737 | 8/1992 | Kenna | 424/9 |

FOREIGN PATENT DOCUMENTS

| | | |
|---|---|---|
| 0136812 | 4/1985 | European Pat. Off. |
| 0186947 | 7/1986 | European Pat. Off. |
| 0233619 | 2/1987 | European Pat. Off. |
| 0292689 | 11/1988 | European Pat. Off. |
| 331616 | 9/1989 | European Pat. Off. |
| 2169598 | 7/1986 | United Kingdom . |
| 8505554 | 12/1985 | WIPO . |
| 9013256 | 5/1990 | WIPO . |

OTHER PUBLICATIONS

Bharadwaj et al., "Characterization of [Dimethyl N,N'-ethylenebis(L-cysteinato) (2-)-S,S] copper (II), Cu(SCH$_2$CH(CO$_2$CH$_3$—)NHCH$_2$—)$_2$, a Stable Cu(II-–Aliphatic Dithiolate", J. Amer. Chem. Soc., 108, (1986), p. 1351.

Bryden et al., "Multinuclear Nuclear Magnetic Resonance Study of Three Aqueous Lanthanide Shift Reagents: Complexes with EDTA and Axially Symmetric Macrocyclic Polyamino Polyacetate Ligands" Anal. Chem. 53 (1981) p. 1418.

Cacheris et al., "Thermodynamic Study of Lanthanide Complexes of 1,4,7-Triazacyclononane-N,N!,N"-triacetic Acid and 1,4,7,10-Tetraazacyclododecane-N,N',N'''-tetraacetic Acid", Inorg. Chem. 26 (1987) p. 958.

Creaser et al., "Synthesis and Reactivity of Aza–Capped Encapsulated Co(III) Ions", J. Amer. Chem. Soc. 104 (1982) p. 6016.

De Cola et al., "Hexaaza Macrocyclic Complexes of the Lanthanides", Inorg. Chem. 25, (1986) pp. 1729–1732.

Delgado, R., and Frausto Da Silva J.J.R., "Metal Complexes of Cyclic Tetra–Azatetra–Acetic Acids", Talanta, 29 (1982) pp. 815–822.

(List continued on next page.)

Primary Examiner—Paul R. Michl
Assistant Examiner—Tae H. Yoon
Attorney, Agent, or Firm—Lyon & Lyon

[57] ABSTRACT

There are provided polychelants and their metal chelates which are useful in diagnostic imaging and in radiotherapy and which comprise a plurality of macrocyclic chelant moieties, e.g, DOTA residues, conjugated to a polyamine backbone molecule, e.g, polylysine. To produce a site-specific polychelate, one or more of the macrocyclic chelant carrying backbone molecules may be conjugated to a site-directed macromolecule, e.g. a protein.

33 Claims, No Drawings

OTHER PUBLICATIONS

DeRiemer et al., "BLEDTA II: Synthesis of a New Tumor-Visualizing Derivative of Co(III)-Bleomycin", Journal of Labelled Compd. Radiopharm., 18 (1981) p. 1517.

Desreux, "Nuclear Magnetic Resonance Spectroscopy of Lanthanide Complexes with a Tetraacetic Tetraaza Macrocycle, Unusual Conformation Properties", Inorg. Chem., 19 (1980) p. 1319.

Gansow, "Diazo Coupling of some Lanthanide Benzo-Cryptattes to Proteins", Inorg. Chimica Acta, 91, (1984) p. 213.

Geue et al., "Metal Ion Encapsulation: Cobalt Cages Derived from Polyamines, Formaldehyde, and Nitromethane" J. Amer. Chem. Soc. 106 (1984) p. 5478.

Hnatowich et al., "The Preparation of DTPA-Coupled Antibodies Radiolabeled with Metallic Radionuclides: an Improved Method", Journal of Immunological Methods, 65, (1983) p. 147.

Hnatowich et al., "Radioactive Labeling of Antibody: A Simple and Efficient Method", Science 220, p. 613.

Krejcarek, G. E. and Tucker, K. L., "Covalent Attachment of Chelating Groups to Macromolecules", Biochemical and Biophysical Research Communications, 77, (1977) p. 581.

Lehn, J. M., "Cryptates: The Chemistry of Macropolycyclic Inclusion Complexes", Accounts of Chemical Research 11, (1978) p. 49.

Magerstadt et al, "Gd(DOTA): An Alternative to Gd(DTPA) as a $T_{1,2}$ Relaxation Agent for NMR Imaging or Spectroscopy", Magnetic Resonance in Medicine, 3 (1986) p. 808.

Manabe et al., "High-level conjugation of chelating agents onto immunoglobulins: use of intermediary poly(L-lysine)-diethylenetriaminepentaacetic acid carrier", Biochimica et Biophysica Acta, 883 (1986) pp. 460–467.

Meares et al, "Conjugation of Antibodies with Bifunctional Chelating Agents: Isothiocyanate and Bromoacetamide Reagents, Methods of Analysis, and Subsequent Addition of Metal Ions", Analytical Biochemistry, 142 (1984) p. 68.

Moi et al., "X-ray Crystal Structure of a Macrocyclic Cooper Chelate Stable Enough for Use in Living Systems: Cooper(II) Dihydrogen 6-(p-Nitrobenzyl)-1,4,8,11-tetraazacyclotetradecane-1,4,8,11-tetraacetate", Inorg. Chem 26 (1987) p. 3458.

Moi et al., "The Peptide Way to Macrocyclic Bifunctional Chelating Agents: Synthesis of 2-p-Nitrobenzyl-1,4,7,10-tetraazacyclododecane-N,N'N'',N'''-tetraacetic Acid and Study of Its Yttrium(III) Complex", (Reprint) J. Amer. Chem. Soc. 110, (1988) p. 6266.

Paik et al, "Factors Influencing DTPA Conjugation with Antibodies by Cyclic DTPA Anhydride", Journal of Nuclear Medicine, 24, (1983) p. 1158.

Russell, C. D. and Speiser, A. G., "Complexes of Technetium with Hydrocarboxylic Acids: Gluconic, Glucoheptonic, Tartaric, and Citric", J. Nucl. Med., 21, (1980) p. 1086.

Shreve, P. and Aisen, A. M., "Monoclonal Antibodies Labeled with Polymeric Paramagnetic Ion Chelates", Magnetic Resonance in Medicine, 3 (1986) p. 336.

Smith, P. H. and Raymond, K. N., "A Lanthanide-Amine Template Synthesis". Preparation and Molecular Structures of $Ln(L)(CH_3CN)(CF_3SO_3)_3$[L=1,9-Bis(-2-aminoethyl)-1,4,6,9,12,14-hexaaxacyclohexadacane n=La, Yb] and $La(en)_4(CH_3CN)$ $(CF_3SO_3)_3$, Inorg. Chem. 24 (1985) p. 3469.

Smith, et al., "Characterization of a Series of Lanthanide Amine Cage Complexes", Inorg. Chem. 27 (1988) p. 4154.

Torchilin et al., "Antibody Activity of the Polymer-Conjugated Antimyosin", Hybridoma, 6 (1987) p. 232.

Unger et al., "Magnetic Resonance Imaging Using Gadolinium Labeled Monoclonal Antibody", Investigating Radiology, 20, (1985) p. 693.

Duncan et al., "Fate of N-(2-hydroxypropyl) methacrylamide copolymers with pendent galactosamine residues after intravenous administration to rats", Biochemica et Biophysica Acta 880, (1986) pp. 62–71.

Vera et al., "Tc-99m-Galactosyl-Neoglycoalbumin: In Vivo Characterization of Receptor-Mediated Binding to Hepatocytes", Radiology 151, (1984) pp. 191–196.

Eckelman et al., "NMR Enhancement with Gd Labeled Antibodies", Radiolabelled Monoclonal Antibodies for Imaging and Therapy ed. S. C. Srivastava, Plenum Publishing Corpn. (1988) pp. 571–579.

Bharadwaj et al., J. Amer. Chem. Soc., 108, 1351 (1986) "Characterization of [Dimethyl N,N'-ethylenebis(-

(List continued on next page.)

OTHER PUBLICATIONS

L-cysteinato) (2-)-S,S] copper (II), Cu(SCH$_2$CH(CO$_2$CH$_3$)NHCH$_2$—)$_2$, a Stable Cu(II-Aliphatic Dithiolate".

Khaw, B. A., Fallon, J. T., Strauiss, H. W. and Haber, E.; Science, 209, 295 (1980) "Myocardial Infarct Imaging of Antibodies to Canine Cardiac Myosin with Indium-111-Diethylenetriamine Pentaacetic Acid".

Lauffer, R. B.; Chemical Reviews, 87, 901 (1987).

Meares, C. F.; and Wensel, T. A.; American Chemical Society; 17; 202 (1984) "Metal Chelates as Probes of Biological Systems".

Moi, M. K., Meares, C. F., McCall, M. J., Cole, V. C. and DeNardo, S. J.; Analytical Biochemistry, 148, 249 (1985) "Copper Chelates as Probes of Biological Systems: Stable Copper Complexes with Macrocyclic Bifunctional Chelating Agent".

Sherry, A. D. et al.; American Chemical Society, 28, 620–622 (1989) "Synthesis and Characterization of the Gadolinium(3+) Complex of DOTA-Propylamide: A Model DOTA-Protein Conjugate".

Sieving, P. F., et al., Bioconjugate Chem., 165–71, (1990) "Preparation and Characterization of Paramagnetic Polychelates and Their Protein Conjugates".

POLYCHELANTS CONTAINING MACROCYCLIC CHELANT MOIETIES

This application is a continuation-in-part of copending application Ser. No. 07/335,162, filed Apr. 7, 1989, now abandoned.

FIELD OF THE INVENTION

This invention relates to bifunctional polychelants, in particular site-directed macromolecular conjugates of macrocyclic chelants, and the chelates and salts thereof and macrocyclic intermediates therefor, and their applications in medicine, including the field of diagnostic imaging. The polychelates are especially suited to enhance images of selected mammalian organs, tissues, cells, and the like, in vivo, using Magnetic Resonance Imaging, X-ray, gamma scintigraphy, and CT scanning, by virtue of their enhanced imaging properties and site specificity. The polychelants are also well suited for metal detoxification, therapeutic delivery of radioisotopes and diagnostic nuclear medicine applications.

BACKGROUND OF THE INVENTION

Medical imaging modalities, such as MRI, X-ray, gamma scintigraphy, and CT scanning, have become extremely important tools in the diagnosis and treatment of illnesses. Some imaging of internal parts relies on inherent attributes of those parts, such as bones, to be differentiated from surrounding tissue in a particular type of imaging, such as X-ray. Other organs and anatomical components are only visible when they are specifically highlighted by particular imaging techniques.

One such technique with potential to provide images of a wide variety of anatomical components involves biotargeting image-enhancing metals. Such a procedure has the possibility of creating or enhancing images of specific organs and/or tumors or other such localized sites within the body, while reducing the background and potential interference created by simultaneous highlighting of nondesired sites.

Researchers have recognized for many years that chelating various metals increases the physiologically tolerable dosage of such metals and so permits their use in vivo to enhance images of body parts (see for example C. D. Russell and A. G. Speiser, J. Nucl. Med., 21, 1086 (1988) and U.S. Pat. No. 4,647,447 (Gries et al.)). However, such simple metal chelate image enhancers, without further modification, do not generally provide any particularly significant site specificity.

The attachment of metal chelates to tissue or organ targetting macromolecules, e.g. biomolecules such as proteins, in order to produce site specific therapeutic or diagnostic agents has been widely suggested.

Many such bifunctional chelating agents, i.e. agents which by virtue of the chelant moiety are capable of strongly binding a therapeutically or diagnostically useful metal ion and by virtue of the site specific macromolecular component are capable of selective delivery of the chelated metal ion to the body site of interest, are known or have been proposed in the literature. Thus for example even relatively early publications in the field of MRI contrast agents, such as GB-A-2169598 (Schering) and EP-A-136812 (Technicare) suggested the use as contrast agents of paramagnetic metal ion chelates of bifunctional chelants.

The attachment of chelant moieties to site-specific macromolecules has been achieved in a number of ways, for example the mixed anhydride procedure of Krejcarek et al. (Biochemical and Biophysical Research Communications 77: 581 (1977)), the cyclic anhydride procedure of Hnatowich et al. (see Science 220: 613 (1983) and elsewhere), the backbone derivatisation procedure of Meares et al. (see Anal. Biochem. 142: 68 (1984) and elsewhere—this is a technique used by Schering in EP-A-331616 to produce site specific polychelates for use as MRI or X-ray contrast agents), and the linker molecule procedure used for example by Amersham (see WO-A-85/05554) and Nycomed (see EP-A-186947 and elsewhere) to produce paramagnetic metal ion chelates of bifunctional chelants for use as MRI contrast agents.

Thus, Krejcarek et al (supra) disclosed how polyaminopolycarboxylic acid (PAPCA) chelants, specifically DTPA (diethylenetriaminepentaacetic acid) could be conjugated to a protein, such as human serum albumin (HSA), by reaction of the triethylamine salt of the PAPCA with isobutylchloroformate (IBCF) and by reacting the IBCF-PAPCA adduct with the protein. Their aim was to attach one radioactive metal per human serum albumin molecule for the purpose of measuring biological function.

Site specific uses of various imaging techniques all require or would be enhanced by use of a multiplicity of the appropriate metal ion conjugated to a site-directed macromolecule. For example, it is believed that a 50% reduction in $T_1$ relaxation time of water protons in a target tissue is the minimum requirement for an effective MRI contrast agent. Considering the affinity of antibodies for their antigens and the concentration of these antigens in the target tissues, it has been calculated that each antibody molecule must carry many paramagnetic centers to bring about these levels of $T_1$ reduction. (see Eckelman, et al., NATO ASI Series, Series A, 152:571 (1988)).

Unger et al. in Investigative Radiology 20:693 (1985) analyzed tumor enhancement for magnetic resonance imaging using an anti-CEA monoclonal antibody conjugated with Gd-DTPA. They found no tumor enhancement when 4 Gd atoms were bound per antibody molecule, and predicted that a far greater ratio of imaging metal atoms per macromolecule would be required to be effective.

Likewise, Schreve and Aisen in Mag. Res. in Medicine 3, 336 (1986), concluded that the concentrations of paramagnetic ion which could be delivered to a tumor using the described technology would result in large doses for humans, making this approach to imaging highly limited in its use.

For site specific image enhancement however it is important that the site specificity of the tissue or organ targetting moiety of such chelates of bifunctional chelants should not be destroyed by conjugation of the chelant moiety. Where the bifunctional chelant contains only one chelant moiety this is not generally a severe problem; however when attempts have been made to produce bifunctional polychelants by conjugating several chelant moieties onto a single site-specific macromolecule, it has been found that not only is the maximum achievable chelant: site-specific macromolecule ratio may be relatively limited but that as the ratio achieved increases the site specificity of the resulting bifunctional polychelant decreases.

Numerous attempts have nonetheless been made to produce bifunctional polychelants with increased numbers of chelant moieties per site-specific macromolecule.

Thus Hnatowich et al. (supra) used the cyclic anhydride of the chelant DTPA to attach it to a protein.

This is a relatively simple one-step synthesis, procedure which as a result has been used by many other researchers. However, due to the presence of two cyclic anhydride groups in the starting material, widespread cross-linking of the macromolecules can lead to the production of conjugates that can not readily be characterized (see Hnatowich et al., J. Immunol. Methods 65:147 (1983)). In addition, this procedure suffers from the same drawback as that for Krejcarek's mixed anhydride method in that the addition of more than a few chelant moieties destroys the site specificity of the macromolecule to which they are linked. (See also Paik et al. J. Nucl. Med. 25:1158 (1983)).

In order to overcome the problems of attaching larger numbers of chelant moieties to a site-specific macromolecule without destroying its site-specificity, i.e. without disturbing its binding site, there have been many proposals for the use of a backbone molecule to which large numbers of chelant moieties can be attached to produce a polychelant one or more of which can then be conjugated to the site-specific macromolecule to produce the bifunctional polychelant.

The by now conventional cyclic anhydride conjugation technique of Hnatowich et al. (supra) has thus been used to produce bifunctional polychelants in which the chelant moieties are residues of open chain PAPCAs, such as EDTA and DTPA, and in which the backbone molecule is a polyamine such as polylysine or polyethyleneimine. Thus for example Manabe et al. in Biochemica et Biophysica Acta 883: 460-467 (1986) reported attaching up to 105 DTPA residues onto a poly-L-lysine backbone using the cyclic anhydride method and also attaching polylysine-polyDTPA polychelants onto monoclonal antibody (anti-HLA IgG1) using a 2-pyridyl disulphide linker achieving a substitution of up to about 42.5 chelants (DTPA residues) per site-specific macromolecule. Torchlin et al. in Hybridoma 6:229-240 (1987) also reported attaching DTPA and EDTA to polyethyleneimine and polylysine backbones which were then attached to a myosin specific monoclonal antibody or its Fab fragment to produce bifunctional polychelants for use in MRI or scintigraphy.

While Manabe and Torchlin have reported the production of bifunctional polychelants, the cyclic anhydride route adopted by Manabe poses cross-linking and hence characterization problems and Torchlin et al in their conclusion doubted that their technique would enable the paramagnetic metal concentration to be increased sufficiently to permit MRI of tumours.

There is thus a continuing need for improved bifunctional polychelants and the present invention resides in the provision of novel and improved bifunctional polychelants, particularly such polychelants that can be produced from relatively non-complex chelant starting materials. More particularly, the present invention resides in the provision of bifunctional polychelants, and their chelates, containing macrocyclic chelant moieties, that is to say chelants which contain at least one macrocyclic structural element which serves at least in part to define the seat for the chelated ion. Macrocyclic chelants, for example 1,4,7,10-tetraazacyclododecane—tetraacetic acid are themselves well known as chelants capable of forming very stable chelate complexes, but they cannot be effectively linked to backbone molecules such as polylysine by the prior art cyclic anhydride (Hnatowich) or mixed anhydride (Krejcarek) procedures.

This invention provides for the first time an efficient and successful means for creating bifunctional poly(-macrocyclic chelants) (BPMCs) as well as the BPMCs and their chelates themselves. Numerous obstacles previously present in creating a biologically functional imaging molecule with a multiplicity of chelating sites have been overcome, and in particular cross-linking of the polychelants has been avoided, allowing for better solubility and better site-specificity, due to the workable size of the bifunctional polychelant.

SUMMARY OF THE INVENTION

The present invention relates to novel compounds useful in image enhancement as well as nuclear medicine. One type of these novel compounds is composed of a backbone molecule to which a multiplicity of macrocyclic chelant moieties are attached. These polychelant compounds and the chelates and salts thereof are here termed magnifiers. The chelant moieties in the magnifiers are capable of chelating metal ions with a high level of stability, and are metallated with the appropriate metal ion(s) to enhance imaging and/or to deliver cytotoxic doses of radioactivity.

These magnifiers can be attached by well-known methods to a site-directed macromolecule, e.g. a protein, to form BPMCs which can enhance imaging and-/or deliver cytotoxic doses of radioactivity to the targeted cells, tissues, organs, and/or body ducts.

As an intermediate in the process of making the magnifiers, alkylhaloformate adducts of macrocyclic chelants are formed and these represent a further aspect of the invention.

The magnifiers are in and of themselves useful entities in medical diagnosis and therapy, due in part to their unique localization in the body. The monomeric chelates presently used for MRI contrast enhancement (e.g., $Gd(DTPA)^{2-}$, $Gd(DOTA)^{1-}$) have in vivo applications related to their specific, rapid biodistribution, localizing these chelates in the extravascular/extracellular spaces of the body. The size of the magnifier, typically greater than 10kD, radically alters the biodistribution of the chelates. The magnifiers remain primarily in the intravascular system, with a diagnostically useful residence time, providing a range of uses from blood pool imaging and volume determination to thrombus detection and angiography. These diagnoses are not readily accessible with an agent which rapidly disperses into the extracellular/extravascular space.

Attachment of the magnifier to a site-directed macromolecule results in even greater in vivo target specificity. The macromolecule is preferably an antibody, other protein or other molecule which will travel in vivo to that site to deliver the chelated metals. In the present invention the capacity of this site-directed macromolecule to travel and/or bind to its target is not compromised by the addition of the chelated metals. The number of chelates per molecule is sufficient to enhance the image of that particular target. The BPMCs are distinct entities, and desireably are substantially non cross-linked.

In one embodiment the magnifiers of the invention can be represented by the formula I $$B(L)_n \quad (I)$$

where B is the residue of a polyamine backbone molecule, typically a molecule containing at least 20 amine groups, each L is independently the residue of a macrocyclic chelant (or a chelate or salt thereof), and n is an integer preferably at least 20, e.g. 20 to 400, preferably 60 to 300, especially 80 to 200, particularly at least 100.

Using this formula for the magnifiers, the corresponding BPMCs of the invention can be represented by the formula II $$T(B'(L)_n)_m \quad (II)$$

where T is the residue of a site-directed macromolecule, each $B'(L)_n$ is independently the residue of a magnifier of formula I, optionally incorporating a residue $X'$ of a linker molecule which serves to link the magnifier to the macromolecule, and m is a positive integer, e.g. 1 to 10, preferably 1,2,3 or 4.

The backbone molecule to which the macrocyclic chelants are bound has a multiplicity of amines. Any backbone with a plurality of amines, preferably primary amines, can be used. This backbone is preferably a homopolymer such as polylysine or polyallylamine, which is capable of providing a large number of primary amines. High conjugation yield results from the method of attachment of the chelating ligands to the backbone.

The linkage between the backbone B and the macrocyclic chelant moiety is preferably via an amide bond, the amide nitrogen deriving from the backbone molecule and the amide carbonyl group deriving from a carboxyl or carboxyl derivative functionality on the macrocyclic chelant. Particularly preferably the macrocyclic chelant is a PAPCA and especially preferably the carboxyl or carboxyl derivative functionality is attached to the or a ring structure of the macrocyclic chelant at a donor ring heteroatom, especially a nitrogen.

Magnifiers and BPMCs can be used in their unmetallated or undermetallated state for absorption of available metal ions in vivo, such as in metal detoxification. Alternatively, magnifiers and BPMCs can be used in their metallated form to deliver chelated metal ions for diagnostic or therapeutic applications.

Metal ions are chosen for chelation by the magnifiers for their ability to perform their diagnostic or therapeutic role. These roles include but are not limited to enhancing images in MRI, gamma scintigraphic or CT scanning, or X-rays, or delivering cytotoxic agents to kill undesirable cells such as in tumors.

For use with radionuclides, such as in nuclear medicine, this invention provides the advantage of tight binding of the radionuclides by the macrocyclic chelants. This allows a more specific image due to lower background levels of the metals.

Preferably, metal incorporation is accomplished prior to attachment of the magnifier(s) to a site-directed macromolecule. The metal is titrated from substoichoimetric levels up to full incorporation, thus eliminating the need for dialysis and extensive chromatographic purification. In this manner significant losses as well as dilution are avoided. Non-specific binding of the metal ions to the macromolecules is also prevented. However, application of the invention to radionuclides with short half-lives may require metallation of the BPMC as a final step, followed by simple rapid purification (e.g. gel filtration) to remove excess unbound radionuclide.

In the BPMC, preferably one or two backbone molecules are linked to the site-directed macromolecule. By limiting the number of magnifiers linked to the macromolecule the pharmacological behavior of the BPMC would be expected to show high target specificity and low non-specific binding.

The BPMCs are capable of containing a large number of macrocyclic chelant moieties. This allows site-specific imaging to be enhanced beyond the levels previously available.

These magnifiers and BPMCs are not only extremely useful for magnetic resonance imaging, they are also useful in other forms of imaging, as well as in nuclear medicine. Osmolality of currently available image enhancing agents contributes to some of the undesirable side effects of these agents, including pain to the patient. By allowing a marked increase in the number of image enhancing chelated metal centres per molecule in solution, this invention allows for a significant decrease in osmolality, while retaining the same level or increasing the level of image enhancement.

The bifunctional poly(macrocyclic chelates) of the present invention have been demonstrated, as set forth in Example 19 below to possess superior biodistribution properties as compared to conventional bifunctional polychelates containing linear, DTPA-based chelant moieties.

DETAILED DESCRIPTION

Backbone Molecule

The magnifiers of the invention are produced by conjugating a plurality of macrocyclic chelants onto a backbone molecule, generally a water-soluble polymer having reactive primary amine groups. The backbone polymer will conveniently have at least 20, preferably at least 60, more preferably at least 100 reactive amine groups. The backbone molecule conveniently is a branched-chained or linear chained, preferably linear-chained, polymer.

Suitable backbone polymers include polypeptides, polyallylamine, poly[N(2-aminoethyl)]methacrylamide, the starburst dendrimers, and polyaminocarbohydrates. Homopolymers are preferred. Most preferred is polylysine, especially poly-L-lysine.

Polyallylamine $[-CH_2CH(CH_2NH_2-HCl)-]_n$ is available commercially from a number of sources including Aldrich Chemical Company (Milwaukee, Wis.) and Polysciences, Inc (Warrington, Pa.). Synthesis of poly[N(2-aminoethyl)]methacrylamide is described in detail in Example 16 below. The starburst dendrimers include polyaminoamido dendrimers (PANAM) and related starburst dendrimers, including the sixth generation dendrimers. Preparation of PANAM and related dendrimers is described by Tomalia et al. in Polymer Journal 17:117 (1985) and in U.S. Pat. No. 4,587,329.

Preferred polyaminocarbohydrates include poly(aminodextran) and chitosan. U.S. Pat. No. 4,699,784 (Shih et al.) describes the preparation of polyaminodextran. Chitosan is commercially available from Sigma Chemical Co. Preparation of N-acyl derivatives of chitosan is described by Moore et al. in Int. J. Macromol. 3:292 (1981).

When the backbone polymer is a polypeptide, amino acid residues having primary amine groups (such as residues of ornithine and lysine) will conveniently constitute at least 50%, preferably at least 80%, more preferably at least 90% of the amino acid residues present in the polypeptide. Any additional amino acid residues will generally not interfere with the water-solubility of the polypeptide. Additional amino acid residues will preferably be polar. Polar amino acids include arginine, glutamic acid, aspartic acid, glutamine and asparagine, in addition to lysine and ornithine. The polypeptide will preferably be free from bonds that provide a fixed, tertiary conformation, such as disulfide bonds. The homopolypeptides homopolylysine and homopolyornithine are preferred.

Numerous methods for making polypeptides are well known in the art; see for example Merrifield in J. Amer. Chem. Soc. 85:214-219 (1963). Moreover, homopolypeptides are available commercially from a number of sources including Sigma Chemical Co. (St. Louis, Mo.) and Aldrich Chemical Company.

Macrocyclic Chelants

The macrocyclic chelant moieties in the polychelants of this invention preferably derive from macrocyclic chelants which have a reactive carboxyl or amine group which is not essential for metal coordination bonding. The reactive group can be one of the groups which in the free chelant can function as a metal coordinating group so long as the backbone conjugated chelant moiety retains the ability to complex metal ions. Alternatively the reactive group can be a substituent of a side chain of the chelant.

More particularly, as used herein, a macrocyclic chelant is defined as a chelant having one continuous, linked, closed backbone consisting of donor atoms, such as for example N, P, B, O, S and As, spaced by carbon atoms e.g. carbons of optionally substituted methylene or cyclic, e.g. aromatic, groups or chains thereof, particularly preferably optionally substituted $C_{2-4}$ alkylene chains. Any of the methylene groups or donor atoms, where permitted by valence conditions, can be substituted so long as the closed chain of the macrocycle remains intact.

In one preferred embodiment of the invention, the macrocyclic chelants are of formula III

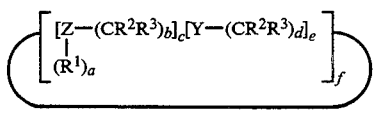
(III)

where a, b, d and e are independently zero or a positive integer, for b or d preferably 1, 2, 3 or 4; c and f are positive integers; the sum of all cs being at least 3, preferably 3, 4 or 5; the sum of b+d is at least 1; each Z is independently a nitrogen, oxygen, sulphur, phosphorus, boron or arsenic, preferably at least two, especially at least 3 of these being nitrogen; each Y is independently an optionally substituted 5 to 7 membered carbocyclic or heterocyclic ring;

$R^1$ where present is independently hydrogen, optionally hydroxylated, optionally alkoxylated alkyl optionally carrying a group CO-G where G is $OR^2$ or $NR^2_2$ and where Z is phosphorus optionally also oxo, at least 3 $Z(R^1)_a$ moieties preferably having Z as nitrogen, a=1 and $R^1$ as an optionally substituted G-CO-alkyl group;

$R^2$ and $R^3$ which may be the same or different each independently is hydrogen, optionally alkoxylated, optionally hydroxylated alkyl, aryl, alkaryl or aralkyl or $R^3$ may also represent or be substituted by a group CO-G; and $NR^2_2$ may also represent a nitrogen-attached optionally substituted 5 to 7 membered heterocyclic ring optionally containing a further nitrogen oxygen, or sulphur ring heteroatom; and where in place of two $CR^2R^3$ groups, separated in either direction by at least one Z group, there may optionally be a bridging structure of formula

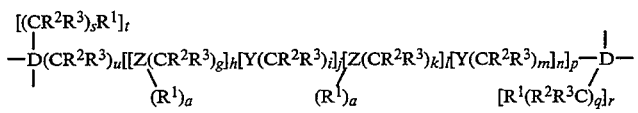

where u, g, h, i, j, k, l, m, n, q, r, s and t is each independently zero or a positive integer, for u, g, i, k and m preferably 1,2,3 or 4; p is a positive integer; $h+l+j+n \geq 1$, preferably $p(h+l) \geq 1$; and each D is independently boron, carbon, nitrogen, phosphorus or PO.

Preferred identities for the ring moieties Y include

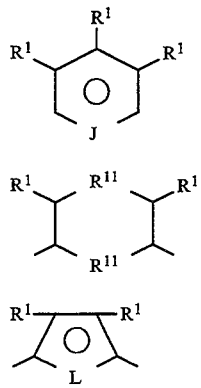

where
J is CH, COH or N;
$R^{11}$ is $CH_2$, CHOH, $NR^1$ O or S; and
L is O or S.

Preferred identities for the heterocyclic moieties $NR^2_2$ include

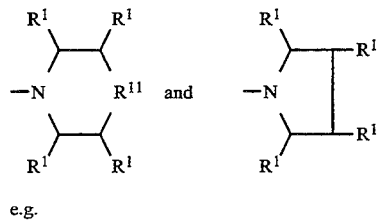

e.g.

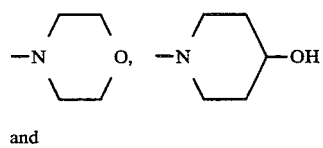

and

-continued

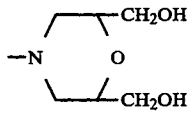

As indicated above, the macrocyclic chelant may include a second "cycle" which is created by linking the branches from two or more backbone atoms.

In the macrocyclic chelants, alkyl and alkylene moieties, unless specified otherwise, preferably contain up to 8 carbon atoms, especially preferably up to 4 carbons. Hydroxy or alkoxy substituted moieties may be mono- or poly-substituted and substitution by both is contemplated. Any aryl moieties are preferably $C_{6-10}$ carbocyclic or 5 or 6 membered heterocyclic rings. In the macrocycle, backbone heteroatoms, e.g. N,P,O and S are preferably separated by 1 to 8, especially preferably 2 to 6 carbon backbone atoms and, as mentioned, the macrocyclic chelant preferably contains at least 3 carboxyl groups or carboxyl derivative groups. Macrocyclic polychelants containing at least three ring nitrogen attached carboxyalkyl, especially carboxymethyl, groups are particularly preferred.

Linkage of the macrocyclic chelant to the backbone molecule may be effected through any reactive group, e.g. an $R^1$ or $R^3$ group, particularly preferably a CO-G group containing $R^1$ group.

Particularly preferably macrocyclic chelants include those of formula IV

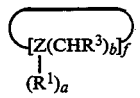

where
each Z is N,O or S, preferably all or all but one Z being N;
each b is independently 2,3 or 4, preferably 2 or 3;
f is 3 or 4, preferably 4;
each $R^1$ is independently hydrogen, $C_{1-3}$ alkyl or an optionally branched, optionally hydroxylated CO-G-alkyl group; and
each $R^3$ is independently hydrogen or a hydroxyalkyl group.

Thus in particular, the macrocyclic chelants include the polyazacycloalkanepolycarboxylates, hexaazamacrocycles (HAMs) and cryptates including sepulchrates and sarcophagines.

Exemplary polyazacycloalkanepolycarboxylates include 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecanetriacetic acid (OTTA), 1,4,7-triazacyclononanetriacetic acid (NOTA) and 1,4,8,11-tetraazacyclotetradecanetetraacetic acid (TETA). Additionally, the novel tetraazacycloalkanepolycarboxylates, DOTA-N(2-aminoethyl)amide and DOTA-N(2-aminophenethyl)amide are also contemplated.

The preparation of the tetraazacycloalkanepolycarboxylate ligands is well known. Synthesis of DOTA is described in U.S. Pat. No. 4,647,447 (Gries et al.) U.S. Pat. No. 4,639,365 (Sherry) and by Desreux et al. in Inorg. Chem. 19:1319 (1980). Additionally, DOTA is available commercially from Parrish Chemical Co., Orem, Utah. Preparation of DO3A is described in EP-A-292689 (Squibb). Desreux, Inorg. Chem., 19:1319 (1980); Bryden et al, Anal. Chem, 53:1418 (1981); Delgardo et al, Talanta, 29:816 (1982); Cacheris et al, Inorg. Chem, 26:958 (1987); Moi et al, Inorg. Chem, 26:3458 (1987) and Meares et al, Acc. Chem. Res., 26:3458 (1987) describe the properties and chemistry of the macrocyclic ligands DOTA, NOTA, TETA and their backbone-derivatized analogs, including the preparation of NOTA and TETA. U.S. Pat. No. 4,678,667 (Meares et al.) teaches the preparation of a number of macrocyclic, side chain-derivatized ligands including DOTA and TETA. Derivatization of DOTA to form DOTA-N(2-aminoethyl)amide and DOTA-N(4-aminophenethyl)amide is described in detail hereinafter in Examples 2 and 3, respectively. The above cited references and all other references mentioned herein are hereby incorporated by reference in their entirety.

The hexaazamacrocycles include the series of $N_6$ macrocyclic chelates described in DeCola et al. in Inorg. Chem., 25:1729 (1986). That article also describes preparation of the HAMs and is incorporated herein by reference in its entirety.

Cryptates are polycyclic ligands which include sepulchrates, sarcophagines and macrocyclic polyethers (crown ethers) and macrobicyclic ligands. Preferred macrocyclic polyether cryptates include side-chain derivatized primary amine and carboxylate cryptates.

The sepulchrates include derivatives of the octaazamacrobicyclic system such as 1,3,6,8,10,13,16,19-octaazabicyclo[6,6,6]eicosane. Primary amine and carboxylate derivatives of these chelates are especially preferred. Synthesis of the chelates, as the cobalt complexes, is described in J. Amer. Chem. Soc., 104:6016 (1982). The sarcophagines include derivatives of the hexaazamacrobicyclic system such as 3,6,10,13,16,19-hexaazabicyclo[6,6,6]eicosane. The bridgehead monoamine derivative is especially preferred. Synthesis of sepulchrates and sarcophagines are described by Creaser et al. in J. Amer. Chem. Soc., 104:6016 (1982) and Geue et al. in J. Amer. Chem. Soc., 106:5478 (1984), respectively. Izatt and Christensen, Eds., Synthetic Multidentate Compounds, Academic Press (1978) and Lehn et al, Acc. Chem. Res., 11:49 (1978) describe synthesis of cryptates. Cotton & Wilkinson "Advanced Inorganic Chemistry" describe a general method of crown ether template synthesis for preparing encapsulating nitrogen-containing macrocycles. Those references are incorporated herein by reference in their entirety.

The products formed by reacting macrocycles containing at least one carboxylate group capable of activation by haloformate are themselves useful intermediates for preparing novel compounds. For example macrocycle dimers can be prepared by reacting said intermediate with a second macrocycle containing a primary amine group, resulting in a dimer linked through an amide moiety.

Metal Ions

Metals that can be incorporated, through chelation, include lanthanides and other metal ions, including isotopes and radioisotopes thereof, such as, for example, Mg, Ca, Sc, Ti, B, V, Cr, Mn, Fe, Co, Ni, Cu, Zn, Ga, Sr, Y, Zr, Tc, Ru, In, Hf, W, Re, Os, Pb and Bi. Particularly preferred radioisotopes of some of the foregoing include $^{153}$Sm, $^{64}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation by polychelants of the invention will be determined by the desired therapeutic or diagnostic application.

Site-Directed Macromolecules

The site-directed macromolecules used in the compositions of this invention can be any macromolecules that are naturally concentrated in a selected target organ, tissue, cell or group of cells, or other location in a mammalian body, in vivo. These can include proteins, peptides, lipoproteins and glycoproteins. Exemplary site-directed proteins include polymerized fibrin fragments (e.g., E$_1$), serum amyloid precursor (SAP) proteins, low density lipoprotein (LDL) precursors, serum albumin, surface proteins of intact red blood cells, receptor binding proteins such as estrogens, liver-specific proteins/polymers such as galactosyl-neoglycoalbumin (NGA) (see Vera et al. in Radiology 151: 191 (1984)) N-(2-hydroxy-propyl)methacrylamide (HMPA) copolymers with varying numbers of bound galactosamines (see Duncan et al., Biochim. Biophys. Acta, 880:62 (1986)), and allyl and 6-aminohexyl glycosides (see Wong et al., Carbo. Res., 170:27 (1987)), and fibrinogen.

The site-directed protein can also be an antibody. The choice of antibody, particularly the antigen specificity of the antibody, will depend on the desired use of the conjugate. Monoclonal antibodies are preferred over polyclonal antibodies.

Human serum albumin (HSA) is a preferred protein for the study of the vascular system. HSA is available commercially from a number of sources including Sigma Chemical Co. Preparation of antibodies that react with a desired antigen is well known. Antibody preparations are available commercially from a variety of sources. Fibrin fragment E$_1$ can be prepared as described by Olexa et al. in J. Biol. Chem., 254:4925 (1979). Preparation of LDL precursors and SAP proteins is described by de Beer et al. in J. Immunol. Methods, 50:17 (1982). The above described articles are incorporated herein by reference in their entirety.

Method of Preparing Complex: General Order

In general, magnifiers are synthesized by conjugating the chelants to the backbone molecule prior to conjugating the backbone molecule to the site-directed macromolecule to produce a bifunctional polychelant. In most cases, the reaction conditions used for joining the chelants to the backbone molecule would denature proteins. Therefore, to preserve its tertiary structure and biological function an antibody or other site-directed protein will not generally be conjugated to a backbone molecule before the chelant groups have been loaded onto that backbone molecule, unless of course this can be done without denaturing the protein. The metal ions can be added to form the metal complex of the polychelants prior to or following conjugation of the magnifier to the site-directed macromolecule. Preferably, the metal will be added prior to conjugation of the magnifier polychelant to most proteins, particularly antibodies, in particular to avoid adventitious binding of the metal to the protein. However, for some metal ions such as radionuclides with a short half-life, metallation will preferably be performed following conjugation, just prior to use.

Linking the Macrocyclic Chelants to the Backbone Molecule

While in general well known methods can be used to join the macrocyclic chelants to backbone molecules, one particularly important aspect of the present invention is that it provides a simple and straightforward means of attaching macrocyclic chelants to backbone polyamine molecules. Thus while for preferred macrocyclic chelants such as DOTA the conventional mixed anhydride and cyclic anhydride conjugation techniques are ineffective, we have found that modifying the mixed anhydride procedure by reacting a polycarboxylic macrocyclic chelant in an anhydrous medium with an amine base of sufficient strength to abstract all the carboxyl protons yields an amine salt which can react with an alkylhaloformate to produce an activated anhydride capable of conjugating to the backbone polyamine without causing the undesired cross-linking associated with prior art bifunctional polychelants. For most macrocyclic chelants tetramethylguanidine or an amine base of similar strength will be the preferred base.

More complex conjugation techniques, involving for example the use of macrocyclic chelants backbone derivatized in a manner analogous to that of Meares et al. (supra) may of course be used but the increased cost and complexity of the overall production makes this a less desireable route. Similarly the chelants can be attached to the backbone polymer by a haloacetylhalide, a phosgene or a thiophosgene method depending on the available reactive group on the chelating agent.

For macrocycles with a pendant carboxylate, including but not limited to DOTA, TETA, TRITA (1,4,7,10-tetraazacyclotridecanetetraacetic acid) and NOTA, one of the coordinating carboxylates can form an entity which can react with a primary amine group of the backbone polymer. Methods of forming a reactive entity from a carboxylate group include the modified mixed anhydride reaction for example using isobutyl-chloroformate (IBCF), or the formation of an "activated ester" using a carbodiimide (DCC or EDAC, cf. Pierce Catalog (1988), p. 252 and 253). Both reaction sequences give rise to a backbone polymer multiply substituted with the macrocyclic chelant moieties through stable amide linkages. The modified mixed anhydride method however is the preferred method for use in joining the carboxylate-containing macrocyclic chelants to the backbone polymer.

The modified mixed anhydride reaction is performed in an anhydrous solvent preferably with a melting point below 5° C., cooled to a temperature not lower than 5° C. or greater than about 55° C. above its freezing point. The solubilization of the chelant in the appropriate solvent is conveniently effected by preparation of the amine salt of the chelant using the amine base in situ.

The choice of base is determined by the pKa of the relevant carboxylates. For most macrocycles, tetramethylguanidine (TMG) is especially preferred. In general, bases will conveniently be selected from those bases whose pKa value exceeds the highest pKa of the macrocyclic chelant by at least 0.5, preferably 0.8, especially preferably at least 1.0. Amine bases having pKa's of at least 11, especially at least 11.3, particularly at least 12, are particularly preferred and besides TMG particular mention may be made of piperidine, quinuclidine and N-ethylpiperidine and more especially DBU (1,8-diazabicyclo[5.4.0]undec-7-ene) and DBN (1,5-diazabicyclo[4.3.0]non-5-ene). Further bases are listed by Martell and Smith in "Critical Stability Constants" Vol. 5, first supplement, Plenum Press, N.Y. 1982.

The appropriate quantity of neat (chilled) alkylhaloformate is now added with stirring and the original temperature of the solvent is maintained by cooling, e.g. by addition of coolant, if required. Isobutylchloroformate is especially preferred. The resulting activated anhydride of the macrocyclic chelant can be reacted with one or more amine-containing macrocycles to form dimers, trimers and/or oligomers, or it can be reacted with the free base form of an amine-containing polymer to form a magnifier polychelant. The magnifier polychelant, for most applications, is metallated at this point and purified by chromatography or crystallization to remove excess metal ions and lower molecular weight metal complexes. For use with target-specific macromolecules the magnifier polychelant or the at least partially metallated form thereof, still containing at least one free amine, is conjugated to the macromolecule, for example by reaction with one of many well-known heterobifunctional coupling agents to effect a link to the macromolecule. In situations where prior metallation is not appropriate, e.g. with radionuclide metal ions with short half-lives, the bifunctional polychelant can be prepared using a metal-free magnifier and coupling as described above, followed by metallation (vide infra) and final rapid, simple purification by chromatography or filtration.

By way of example, attachment of DOTA to polylysine by a preferred modified mixed anhydride method is described below in detail in Example 12.

The macrocyclic chelants can also be linked to the backbone polymer through a non-coordinating primary amine group. Macrocyclic chelants having a non-coordinating primary amine group include primary amine side-chain derivatized DOTA macrocycles, primary amine-derivatized DO3A, and primary amine-derivatized hexaaza and octaaza macrocycles and macrobicycles (the HAMs, sepulchrates and sarcophagines) as well as the broad class of derivatized crown ether cryptates.

The non-coordinating primary amine group on these chelants can be reacted with a haloacetylhalide under well known conditions to form a haloacetamide. The haloacetamide can react with a primary amine of the backbone polymer to form a stable amide linkage between the chelant and the polymer. The haloacetylhalide method described in De Riemer et al, J. Labelled Compd. Radiopharm., 18:1517 (1981) can be used to join aminecontaining chelants to the backbone polymer.

Amine groups on a macrocyclic chelant can also be reacted with phosgene to generate a reactive isocyanate group, or with thiophosgene to generate a reactive isothiocyanate group. Those groups can react with a primary amine of the backbone polymer to form a stable urea or more stable thiourea linkage, respectively, between the ligand and the backbone polymer. Gansow, Inorg. Chimica Acta, 91:213 (1984) and Moi et al, J. Amer. Chem. Soc., 110:6266 (1988) describe methods of linking chelants to proteins having an amine group through formation of the isocyanate or isothiocyanate moieties using the phosgene or thiophosgene methods, respectively. See also Desreux, Inorg. Chem., 19:1319 (1980); Bryden et al, Anal. Chem, 53:1418 (1981); Delgardo et al, Talanta, 29:815 (1982); Cacheris et al, Inorg. Chem., 26:958 (1987); Moi et al, Inorg. Chem, 26:3458 (1987) and Meares et al, Acc. Chem. Res., 26:3458 (1987).

Metallation

As indicated earlier the choice of metal ions to be chelated by the polychelants of the invention depends upon the diagnostic or therapeutic technique for which the resulting polychelate is to be used. For MRI, the metal ions should be paramagnetic, and preferably non-radioactive. For X-ray and ultrasound imaging, heavy metal ions, e.g. with atomic numbers of at least 37, preferably at least 50, should be used, again preferably nonradioactive species. For scintigraphy or radiotherapy the metal ions should of course be ions of radioactive isotopes.

Methods of complexing metal ions with chelants and polychelants are within the level of skill in the art. Each of the metals used can be incorporated into a macrocyclic chelant moiety by one of three general methods: direct incorporation, template synthesis and/or transmetallation. Direct incorporation is preferred.

The metal ions Fe(III), Cr(III), Mn(II), Hg(II), Pb(II), Bi(III) and the lanthanides can be directly incorporated into polyaminopolycarboxylates by the following general procedure. A water-soluble form of the metal, generally an inorganic salt, is dissolved in an appropriate volume of distilled, deionized water. The pH of the solution will be below 7. An aqueous solution containing an equimolar amount of the polychelant is added to the metal solution at room temperature while stirring. The pH of the mixture is raised slowly by addition of base, typically 0.1 M NaOH, until the donor groups of the polychelant are deprotonated, generally in the pH range of 7 to 9, depending on the chelant moieites. Particular care must be taken with the lanthanide ions to maintain the pH below 8 to avoid precipitation of the metal hydroxide. Metal incorporation into DOTA derived and related macrocylic chelant moieties will normally be a slow process, as described in the references cited below. Specific examples of the procedure are contained in the Examples hereto and in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 3:145 (1989). The above references are incorporated herein by reference in their entirety.

Direct incorporation of Hf, Zr, W, Hg and Ta can be performed according to well known methods. See, for example, U.S. Pat. No. 4,176,173 (Winchell).

Transmetallation is useful when the metal ion needs to be reduced to a more appropriate oxidation state for the donor atoms of the chelant moiety to bind. For example, to incorporate $^{99M}Tc$ or $^{186/188}Re$, the metal ion must be reduced to Tc(V) or Re(V) by the use of reducing agents such as $SnCl_2$ or cysteine by well known methods. This method requires formation of an intermediate complex. A typical example is the reduction of $^{99M}Tc$ with Sn in the presence of a weakly coordinating ligand such as glucoheptonate prior to complexation with chelants such as DOTA. These methods are well known in the radiopharmaceutical art. $^{67}Cu$ utilizes tetraamine chelates such as tet A or tet B (see Bhardaredj et al., JACS, 108:1351 (1986)) to stabilize Cu(II) for reaction with stronger-binding chelants.

Template synthesis can be performed by the method described by Smith et al. in Inorg. Chem., 24:3469 (1985) and 27:4154 (1988). In the case of the HAM systems, the metal ion is incorporated into the macrocyclic chelant by building the chelant around the metal ion via template synthesis. Well-known template synthesis methods are described by Smith et al. (Supra) for lanthanide template syntheses. The sepulchrate and sarcophagine macrobicyclic chelants may be similarly prepared by a template synthesis around Co. The Co is removed by reduction to Co(II) and extraction with 15 M HBr. The metal-free chelant may then be metallated via reaction with a simple metal salt by refluxing in methanol, or by transmetallation from a donor complex such as glucoheptonate, ascorbate, acetate or citrate salts. Use of trillate and/or perchlorate salts are preferred.

The broad class of crown ethers and cryptates, especially those containing N, O, and S, can be metallated in a similar fashion using one or more of the methods described above.

Attaching Backbone to Protein

Methods for attaching backbone polymers to antibodies and other proteins are within the level of skill in the art. Such methods are described in Pierce 1989 Handbook and General Catalog and the references cited therein, Blatter et al, Biochem., 24:1517 (1985) and Jue et al, Biochem., 17:5399 (1978). The references cited above are incorporated herein by reference in their entirety.

Formulation

The metal chelates of the polychelants of the invention, especially the bifunctional polychelants but optionally also the magnifier polychelants, may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.02 to 1.2 mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

For X-ray applications, to extend the photon energy range over which the polychelates of the invention are optimally effective the polychelates used may be of two or more different metals, either as mixtures of homopolychelates or as a heteropolychelate.

The compounds of the present invention may be formulated with conventional pharmaceutical or veterinary aids, for example stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA-bisamide or non-complexed magnifier polychelant) or calcium chelate complexes (as for example calcium DTPA, CaNaDTPA-bisamide, calcium–magnifier polychelant or CaNa salts of magnifier polychelants), or, optionally, additions (e.g., 1 to 50 mole percent) of calcium or sodium salts (for example, calcium chloride, calcium ascorbate, calcium gluconate or calcium lactate combined with metal chelate complexes of magnifier ligands, and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavoring.

For MRI and for X-ray imaging of some portions of the body the most preferred mode for administering metal chelates as contrast agents is parenteral, e.g., intravenous administration. Parenterally administrable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Viewed from a further aspect the invention provides an image enhancing or therapeutic composition comprising a metal chelate of a polychelant of the invention or a salt thereof together with at least one pharmaceutical carrier or excipient.

Viewed from a still further aspect the invention provides the use of a polychelant according to the invention or a chelate or salt thereof for the manufacture of an image enhancing contrast medium or a therapeutic composition.

Viewed from another aspect the invention provides a method of generating an image of a human or non-human animal, especially mammalian, body which method comprises administering to said body an image enhancing amount of a polychelate according to the invention or a salt thereof and thereafter generating an image e.g. an MR, X-ray, ultrasound or scintigraphic image, of at least a part of said body.

Viewed from a still further aspect the invention provides a method of radiotherapy of the human or animal body said method comprising administering to said body a therapeutically effective amount of a radioactive metal chelate of a polychelant according to the invention.

Viewed from a yet still further aspect the invention provides a method of producing a polychelant according to the invention or a chelate thereof, said method comprising conjugating to a backbone polyamine a plurality of macrocyclic chelants, optionally conjugating the resulting polychelant to a site-specific macromolecule, and optionally metallating said polychelant before or after conjugation to a said macromolecule.

Viewed from another aspect the invention provides a detoxification composition comprising a polychelant according to the invention or a weak chelate complex or salt thereof with physiologically tolerable counterions, together with a pharmaceutical carrier or excipient.

Viewed from a still further aspect, the invention provides a method of metal detoxification comprising administering to a human or non-human animal a detoxifying amount of a polychelant according to the invention or a weak chelate complex or salt thereof with physiologically tolerable counterions.

This invention is further illustrated by the following specific but non-limiting examples. Temperatures are given in degrees Celsius and concentrations as weight percentages unless otherwise specified.

EXAMPLE 1

Preparation of DOTA Carboxycarbonic Anhydride

DOTA(0.808g, 2.0 mmol) was suspended in 5.0 ml of anhydrous acetonitrile. Tetramethylguanidine (1.00 ml, 8.0 mmol) was added and the mixture stirred under an atmosphere of nitrogen for about 5 minutes at ambient temperature until the DOTA was dissolved. The resulting solution was cooled to $-25°$ C. under an atmosphere of nitrogen and stirred while adding 0.260 ml (2.0 mmol) of isobutylchloroformate (IBCF), slowly over 5 minutes. The resulting slurry was stirred 1 hour at $-25°$ C.

EXAMPLE 2

Preparation of DOTA-N(2 -aminoethyl) amide

To the cold slurry from Example 1 was added a solution of mono-BOC-ethylenediamine (0.320g, 2 mmol) in 2 ml acetonitrile and the mixture stirred 6 to 12 hours at ambient temperature. The mixture was brought to 20 ml with $H_2O$, treated with 6 ml of concentrated HCl, and then stirred overnight to effect removal of the protecting group. The solution was evaporated to dryness. The residue was purified by ion exchange chromatography on DOWEX AGI-X8 resin. Evaporation of the appropriate fractions afforded 0.35g of a semi-crystalline glass. $^1H$ NMR demonstrated the expected product, as well as some residual acetate (from chromatography).

EXAMPLE 3

Preparation of DOTA-N(4-aminophenethyl)amide

To the cold slurry from Example 1 is added a solution of 4-nitrophenethylamine (0.332g, 2 mmol) in 4.0 ml acetonitrile. The mixture is stirred 6 to 12 hours at ambient temperature. After evaporation to dryness, the residue is redissolved in water and pH adjusted to 10.5 with NaOH to form a mixture which is extracted with ethyl acetate to remove unreacted amine. The product, DOTA-N-(4′-nitrophenethyl)amide, is isolated by ion exchange chromatography on DOWEX AGI-X8 resin. Following evaporation of the appropriate fractions, the residue is dissolved in water in a Parr reactor, and 0.1 g of 5% palladium on activated carbon is added to form a reaction mixture. The reaction mixture is hydrogenated at 30-40 psi until the pressure ceases to drop. The product is isolated by filtering off catalyst and evaporating the filtrate to dryness.

EXAMPLE 4

Activation of Amino Group of DOTA-N(2--aminoethyl)amide with Thiophosgene-Conversion to Isothiocyanate Groups An aqueous solution of the product prepared in Example 2 is added to an equal volume of chloroform containing thiophosgene and sodium bicarbonate, each of which is in four-fold molar excess with respect to the target amino group. The mixture is stirred vigorously for 1-2 hours, and the phases are separated. The aqueous phase is washed with chloroform, and then it is evaporated to dryness. The resultant solid product is washed with ethanol and dried in vacuo.

The procedure is repeated, substituting the product of Example 3 for the product of Example 2.

EXAMPLE 5

Activation of Amino Group of DOTA-N(2-Aminoethyl)Amide with Bromoacetyl Chloride-Conversion to Bromoacetamide Groups An aqueous solution of the product prepared in Example 2 (20 mg/ml) which also contains triethylamine (20 mg/ml) is treated with an equal volume of a chloroform solution of bromoacetyl chloride (30 mg/ml), and the two-phase mixture is stirred vigorously for 1-2 hours. Water is added, to double the volume of the aqueous phase, and the mixture is extracted with ethyl acetate. The aqueous phase is evaporated to dryness and the residue triturated with acetone and dried in vacuo.

The procedure is repeated, substituting the product of Example 3 for the product of Example 2.

EXAMPLE 6

Coupling of DOTA-Isothiocyanate Derivates to Poly-L-Lysine (degree of polymerization approximately=100)

A solution of poly-L-Lysine (20 mg/ml) in 0.1M sodium bicarbonate, pH 9.5 is treated with a four-fold molar excess with respect to ($\epsilon$-amino groups) of the activated chelant prepared in Example 4. The mixture is stirred overnight at ambient temperature. The product is freed of excess ligand by size exclusion chromatography on Sephadex G-25 and isolated by lyophilization of the appropriate fractions.

EXAMPLE 7

Coupling of DOTA-Bromoacetamide Derivates to Poly-L-Lysine (degree of polymerization=100)

A solution of poly-L-lysine (20 mg/ml) in 0.1M sodium bicarbonate, pH 9.5 is treated with a four-fold molar excess with respect to (ε-amino) groups of the activated chelant prepared in Example 5. The mixture is stirred overnight at ambient temperature. The product is freed of excess chelant by size exclusion chromatography on Sephadex G-25 and isolated by lyophilization of the appropriate fractions.

EXAMPLE 8

Preparation of the Gadolinium Complexes of Thiourea-and Glycinamide-linked Polychelates A sample of one of the polychelant prepared in Examples 6 or 7 is dissolved in an aliquot of 50.1 mM $GdCl_3$ in 0.1 N HCl which contains 5% less than the stoichiometric amount of gadolinium. The pH is adjusted to 7 and the absence of free gadolinium verified by testing with arsenazo(III). While maintaining the pH of the solution at between 6 and 7 by addition of 5 N NaOH, aliquots of 50.1 mM $GdCl_3$ containing 0.5–1.0% of the stoichiometric amount of gadolinium are added at one hour intervals until the solution tests positive for free gadolinium. Aliquots of 0.1–0.5% of the original amount of polychelate are added when there is a large excess of free gadolinium at the time of the first positive test. The solution is stirred overnight. The gadolinium polychelate is freed of unbound gadolinium and other salts by gel filtration (Sephadex G-25) and isolated by lyophilization of the appropriate fractions.

EXAMPLE 9

Activation of Human Serum Albumin (HSA)

HSA contains one native thiolate group. This group was blocked by alkylation as described below. 50 ml of 0.05M Tris-HCl, pH 7.3 was adjusted to pH 8.0 using 1.0M Tris base. HSA (1g, 15 μmol) was added to the solution. After stirring until homogeneous, the flask containing the solution was purged with dry nitrogen, sealed with a septum and wrapped in aluminum foil to exclude light.

A solution of iodoacetamide (15 mg, 80 μmol) in 4.0 ml of 1N NaOH was added dropwise by using a syringe inserted through the septum. The resulting reaction mixture was stirred for 45 minutes at ambient temperature in the dark. The reaction mixture was dialyzed against 3.5 liters of 0.05M sodium bicarbonate, pH 8.0, for 12 hours, with a buffer change at 6 hours. The dialysate was lyophilized to dryness to form a white fibrous mass.

The absence of free thiols in the preparation was demonstrated by the method of Ellman (see Arch. Biochem. Biophys. 74: 443 (1958)). The purity of the preparation was determined by measuring the specific absorbance of a 1 mg/ml solution of the product at 280 nm (1 cm path). The analysis showed that a purity of 99% with yield of 0.903g was obtained.

100 mg of the above thiol-blocked HSA was dissolved in 50 ml of 60 mM triethanolamine, 7 mM monopotassium phosphate, 100 mM NaCl, 1 mM EDTA, pH 8.0. The solution was degassed for 10 minutes by stirring under vacuum, then covered with an atmosphere of nitrogen in a septum-sealed flask. After cooling the flask in an icebath, a solution of 2-iminothiolane (8.5 mg) in 100 μl of 1M triethanolamine, pH 8.0 was added to the flask by syringe. The mixture was stirred for about 90 minutes at 0°–4° C. After overnight dialysis against 3.5 liters of 0.08M sodium phosphate, 0.5 mg/ml; EDTA, pH 8.0 with frequent buffer changes, spectrophotometric analysis by the method of Ellman demonstrated the presence of 2.7 thiols per mole of HSA.

EXAMPLE 10

Activation of Gadolinium Polychelates for Coupling to HSA

A 200 mg sample of one of the polychelates prepared in Example 8 is dissolved in 20 ml of 0.008M $Na_2HPO_4$, pH 8. A solution of 16 mg of succinimidyl-4-(N-maleimidomethyl)cyclohexane-1-carboxylate (SMCC) in 3 ml DMSO is added dropwise to form a mixture. The mixture is stirred 30 minutes at ambient temperature to form a solution. The resulting solution is dialyzed for 12 hours against 4L $H_2O$ with a single change at 6 hours to remove excess SMCC.

EXAMPLE 11

Coupling of Gadolinium Polychelates to HSA

The solutions prepared in Examples 9 and 10 are combined and stirred for 4 hours to form a mixture. The mixture is lyophilized. The resultant solid is dissolved in 10 ml $H_2O$ and dialyzed 6 hours against $H_2O$. The dialysate is chromatographed on Sephacryl S-300. The fractions with significant absorbance at 280 nm are pooled and lyophylized. A sample of this solid is dissolved in water (1 mg/ml) and assayed for HSA (using a spectrophotomer and measuring absorbance at 280 nm) and Gd (using directly coupled plasma atomic absorption (DCP-AA)) to determine the number of metal ions bound per mole HSA.

EXAMPLE 12

Preparation of Polylysine-polyDOTA

A solution of 100 mg of poly-L-lysine (degree of polymerization=103) in 6.0 ml of 0.1N sodium bicarbonate, pH 9.0, was cooled to 0° C. in an ice/water bath and stirred while adding the cold slurry from Example 1, slowly over 5 minutes. The resulting solution was stirred at ambient temperature for 6 hours. The acetonitrile was largely removed by rotary evaporation at 60° C. for 30 minutes. The resulting aqueous solution was dialysed in a 12,500 MW cutoff dialysis sack for about 6 hours at ambient temperature against 3.5 liters of 0.02M oxalic acid, pH 2.0. The dialysis solution was changed to 0.05M sodium bicarbonate, pH 8.0 and dialyzed overnight. The dialysate was removed, lyophilysed to dryness to produce 183 mg of a white powder. Analysis by $^1$H-NMR demonstrated 0.68 DOTA groups per lysine residue, indicating that 68% of the lysine ε-amines were acylated.

EXAMPLE 13

Preparation of Gd(Polylysine-polyDOTA)

A 5.0 ml aliquot of 50.1 mM $GdCl_3$ in 0.1N HCl was added to 300 mg of polylysine-polyDOTA prepared as described in Example 12 to form a mixture. The mixture was stirred until homogeneous and the pH adjusted to 7 to form a solution which tested negative for free gadolinium. While maintaining the solution at a pH of from 6 to 7 by addition of 5 N NaOH, additional 0.5 ml aliquots of 50.1 mM $GdCl_3$ were added at one hour intervals until the solution tested positive for free gadolinium. Aliquots of polylysine-polyDOTA were added when there was a large excess of free Gd. The solution was stirred overnight, followed by purification by gel filtration on Sephadex G-25 to remove unbound gadolinium and other salts. Lyophilization afforded 360 mg of an off-white amorphous powder.

EXAMPLE 14

Preparation of Gd(Polylysine-polyDOTA) for Coupling to HSA

A 200 mg sample of the polychelate prepared in Example 13 was dissolved in 20 ml of 0.008 M $Na_2HPO_4$, pH 8. A solution of 16 mg SMCC in 3 ml DMSO was added dropwise to form a mixture. The mixture was stirred 30 minutes at ambient temperature to form a solution. The resulting solution was dialyzed for 12 hours against 4L $H_2O$ with a single change at 6 hours to remove excess SMCC.

EXAMPLE 15

Coupling of Gd(Polylysine-polyDOTA) To HSA

The solutions prepared in Examples 9 and 14 were combined and stirred for 4 hours. The mixture was lyophilized. The resultant solid was dissolved in 10 ml $H_2O$ and dialyzed 6 hours against $H_2O$ to remove buffer salts. The dialysate was chromatographed on Sephacryl S300. The fractions absorbing significantly at 280 nm were pooled and lyophilized to yield 293 mg of fibrous white solid. A sample of this solid was dissolved in water (1 mg/ml) and assayed for HSA ($A_{280}$) and Gd (by DCP-AA analysis) to determine the number of metal ions bound per HSA (65). HPLC analysis of a more concentrated sample (30 mg/ml) with detection of Gd species by fluorescence excitation/emission demonstrated that less than 0.5% of Gd was present as Gd[DOTA]or other monomeric species.

EXAMPLE 16

Synthesis of poly[N(2-aminoethyl)methacrylamide]-Backbone Polymer

To 0.5g of poly(methylmethacrylate) (degree of polymerisation n=120) in a 250 ml round bottom flask is added a mixture of 90g of ethylene diamine and 50 ml of methanol. The suspension is heated to 65° C. under a condenser with stirring. The suspension becomes homogeneous in about 1 hr. $^1H$ NMR analysis of an aliquot after 24 hours shows the appearance of non-equivalent methylene resonances in the ethylene diamine fragment, indicating mono-amide formation (approximately 30%). Stirring at 65° C. is continued. Completion is projected to be at about 80 hours.

EXAMPLE 17

Formulation of Gd(Polylysine-polyDOTA)-HSA Conjugate

The composition prepared in Example 15 is formulated for use in MRI by dissolving the solid material in deionized water to give a concentration of 1.0-500.0 mM Gd, the osmolality and pH adjusted to within physiologically tolerable limits, and the solution sterilized.

EXAMPLE 18

Use of Gd(Polylysine-polyDOTA)-HSA Conjugate

The formulation prepared in Example 16 is used to diagnose patients with a variety of intra vascular-related disease states by injection into the patient, followed by MRI scanning of the potentially affected area.

EXAMPLE 19

Improved biodistribution

Using chelated $^{153}Gd$ the biodistribution and body retention of gadolinium (polylysine-polyDOTA)-HSA and gadolinium (polylysine-polyDTPA)-HSA have been compared giving ADME results (% of total dose) as follows:

| | DTPA | | DOTA | |
|---|---|---|---|---|
| ORGAN | 24 HRS | 7 DAY | 24 HRS | 7 DAY |
| Liver | 28 ± 2 | 22 ± 1 | 13 ± 1 | 8 ± 3 |
| Kidneys | 3 ± 0 | 2 ± 0 | 8 ± 1 | 2 ± 1 |
| Blood | 37 ± 9 | 0 | 12 ± 1 | 0 |
| Urine | 10 ± 3 | 25 | 36 ± 10 | 47 ± 10 |
| Faeces | 1 ± 3 | 4 | 1 ± 1 | 17 ± 7 |

The Gd(polylysine-polyDTPA)-HSA was prepared from poly-L-lysine (degree of polymerization 105), via polylysine-polyDTPA (88% acylation of ε amines by DTPA).

We claim:

1. A polychelant comprising
   (a) a backbone moiety which is a molecule having a multiplicity of amine groups, and
   (b) bonded to said backbone moiety through its amine groups a plurality of macrocyclic chelant moieties capable of complexing metal ions,
   a metal chelates and salts of said polychelant compound.

2. A polychelant compound according to claim 1, wherein said molecule contains at least 20 amine groups.

3. A polychelant compound according to claim 1, wherein said molecule contains 20 to 400 amine groups.

4. A polychelant compound according to claim 1, wherein said molecule contains 60 to 300 amine groups.

5. A polychelant compound according to claim 1, wherein said molecule contains 80 to 200 amine groups.

6. A polychelant compound according to claim 1, wherein said molecule contains at least 100 amine groups.

7. A compound according to claim 1 of formula I $$B(L)_n \qquad (I)$$

where B is a said backbone moiety, n is an integer having a value of at least 20, and each L is independently the residue of a macrocyclic chelant, or a chelate or salt thereof.

8. A compound according to claim 7 having a non-crosslinked structure.

9. A compound according to claim 7 wherein n is at least 60.

10. A compound according to claim 7 wherein n is at least 80.

11. A compound according to claim 7 wherein n is at least 100.

12. A polychelant compound according to claim 1, wherein said backbone and chelant moieties are linked by amide groups wherein the amide nitrogen is derived from an amine group in said backbone moiety and the amide carbonyl group is derived from a carboxyl group or carboxyl derivative in one of said macrocyclic chelant moieties.

13. A compound according to claim 12 wherein the macrocyclic chelant moieties are linked to said backbone moiety by optionally substituted alkylene groups bonded to the carbonyl groups of said amide group and to donor heteroatoms of the macrocycle skeletons of said chelant moieties.

14. A compound according to claim 1 wherein at least some of said chelant moieties are unmetallated.

15. A compound according to claim 1 wherein at least some of said chelant moieties are metallated by metal ions selected from the group consisting of the paramagnetic ions of Fe, Mn, Co and the lanthanides.

16. A compound according to claim 1 wherein at least some of said chelant moieties are metallated by metal ions selected from the group consisting of the ions of Hf, W, Bi, Hg, Os, Pb, Zr and the lanthanides.

17. A compound according to claim 1 wherein at least some of said chelant moieties are metallated by metal ions selected from the group consisting of the ions of $^{111}$In, $^{99m}$Tc, $^{88}$Y, $^{186}$Re, $^{188}$Re, and $^{203}$Pb.

18. A compound according to claim 1 wherein at least some of said chelant moieties are metallated by metal ions selected from the group consisting of the ions of $^{186}$Re, $^{188}$Re, $^{90}$Y, $^{64}$Cu, $^{67}$Cu, $^{68}$Ga, $^{211\text{-}214}$Bi, and $^{153}$Sm.

19. A compound according to claim 1 wherein said backbone moiety is the residue of a backbone polymer containing a plurality of primary amine groups.

20. A compound according to claim 19 wherein said backbone moiety is the residue of a polymer selected from the group consisting of polypeptides, polyallylamine, poly[N(2-aminoethyl)]methacrylamide, the starburst dendrimers, and polyaminocarbohydrates.

21. A compound according to claim 1 wherein said macrocyclic chelant moieties are residues of macrocyclic chelants of formula III

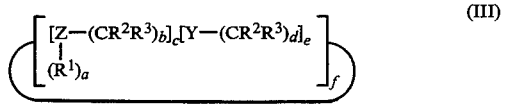

where
a, b, d and e are independently zero or a positive integer; c and f are positive integers, the sum of all cs being at least 3; the sum of b+d is at least 1; each Z is independently a nitrogen, oxygen, sulphur, phosphorus, boron or arsenic; each Y is independently an optionally substituted 5 to 7 membered carbocyclic or heterocyclic ring;
$R^1$ where present is independently hydrogen, optionally hydroxylated, optionally alkoxylated alkyl optionally carrying a group CO-G where G is $OR^2$ or $NR^2_2$ and where Z is phosphorus optionally also oxo;
$R^2$ and $R^3$ which may be the same or different each independently is hydrogen, optionally alkoxylated, optionally hydroxylated alkyl, aryl, alkaryl or aralkyl or $R^3$ may also represent or be substituted by a group CO-G; and $NR^2_2$ may also represent a nitrogen-attached optionally substituted 5 to 7 membered heterocyclic ring optionally containing a further nitrogen, oxygen or sulphur ring heteroatom; and where in place of two $CR^2R^3$ groups, separated in either direction by at least one Z group, there may optionally be a bridging structure of formula

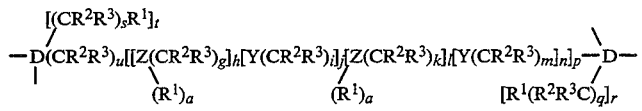

where u, g, h, i, j, k, l, m, n, q, r, s and t is each independently zero or a positive integer; p is a positive integer; $h+l+j+n \geq 1$; and each D is independently boron, carbon, nitrogen or phosphorus or PO.

22. A compound according to claim 1 wherein said macrocyclic chelants are selected from the group consisting of the residues of polyazacycloalkanepolycarboxylates, derivatized crown ethers, derivatized hexaazamacrocycles (HAMs), and derivatized cryptates including sepulchrates and sarcophagines.

23. A compound according to claim 1 wherein said macrocyclic chelants are selected from the group consisting of the residues of 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetradecanetetraacetic acid (TETA), DOTA-N(2-aminoethyl)amide and DOTA-N(2-aminophenethyl)amide.

24. A compound according to claim 1 comprising at least one said macrocyclic chelant-carrying backbone moiety conjugated to a macromolecule, or a chelate or salt thereof.

25. A compound according to any one of claims 7 to 19 and 1 comprising a site-directed macromolecule capable of travelling to or binding specifically to a targeted cell or cells, tissue, organ, or other location in a mammalian body having conjugated thereto 1,2,3 or 4 said macrocyclic chelant moiety carrying backbone moieties, or a chelate or salt thereof.

26. A compound according to claim 24 wherein said macromolecule is selected from the group consisting of antibodies specific for a desired antigen, polymerized fibrin fragments, serum amyloid precursor proteins, low density lipoprotein precursors, serum albumin, surface proteins of intact red blood cells, liver-specific macromolecules, receptor binding proteins and fibrinogen.

27. A compound according to claim 26 wherein said macromolecule is a monoclonal antibody specific for a desired antigen.

28. A compound according to claim 26 wherein said macromolecule is bound to said backbone moieties by heterobifunctional linking agents bonded via reactive linking groups selected from the group consisting of amide, maleamide, disulfide, thiourea, isothiocyanate, and ester.

29. A polychelant compound formed by a process comprising the following steps:
(a) dispersing a carboxylic macrocyclic chelant in a polar anhydrous solvent;

(b) adding a base with a pKa sufficient to remove all carboxyl protons to create an amine salt of the said chelant soluble in said solvent;

(c) chilling the reaction mixture to between about 5° C. and 55° C. above the freezing point of the solvent;

(d) adding a substantially equimolar amount of chilled alkylhaloformate under anhydrous conditions while approximately maintaining the temperature of step (c) for a period of time sufficient for substantially complete reaction to form a slurry containing the mixed carboxycarbonic anhydride of said chelant; and (e) slowly adding the slurry to a solution of the free base form of a polymer carrying a plurality of free amines.

30. A polychelate compound being the product of metallating a polychelant produced according to claim 29 after step (e) thereof.

31. A polychelate compound according to claim 29, or a polychelate compound according to claim 30, formed using dry acetonitrile, dimethylacetamide, or dimethylformamide as the solvent of step (a).

32. A polychelant compound according to claim 29, or a polychelant compound according to claim 30, using tetramethylguanidine, 1,5-diazabicyclo[4.3.0]non-5-ene, or 1,8-diazabicyclo[5.4.0]undec-7-ene as the base of step (b).

33. A polychelant compound according to claim 29, or a polychelant compound according to claim 30, formed using isobutylchloroformate as the alkylhaloformate of step (d).

* * * * *